United States Patent [19]

Rowland

[11] Patent Number: 5,091,560

[45] Date of Patent: Feb. 25, 1992

[54] METHOD FOR SYNTHESIZING ACYLOXYCARBOXYLIC ACIDS

[75] Inventor: Richard R. Rowland, Danville, Calif.

[73] Assignee: The Clorox Company, Oakland, Calif.

[21] Appl. No.: 635,409

[22] Filed: Dec. 21, 1990

Related U.S. Application Data

[63] Continuation of Ser. No. 409,279, Sep. 19, 1989, abandoned, which is a continuation of Ser. No. 167,544, Mar. 14, 1988, abandoned.

[51] Int. Cl.$^5$ ............................................. C07C 69/66
[52] U.S. Cl. ..................................... 560/185; 560/57; 560/58; 560/60; 560/266; 558/6; 558/24; 558/28; 558/37; 558/46; 558/47; 558/56; 558/58; 558/268; 558/269; 558/271; 260/410.5; 260/410.9 R
[58] Field of Search ............... 560/266, 57, 58, 60, 560/185; 558/6, 24, 28, 37, 46, 47, 56, 58, 268, 269, 271; 260/410.5, 410.9

[56] References Cited

U.S. PATENT DOCUMENTS

| | | | |
|---|---|---|---|
| 2,290,128 | 7/1942 | Loder | 560/189 |
| 2,290,881 | 7/1942 | Katzman | 560/252 |
| 2,350,964 | 6/1944 | Loder | 560/186 |
| 2,357,594 | 9/1944 | Loder | 560/186 |
| 2,388,164 | 10/1945 | Loder | 560/186 |
| 2,464,992 | 3/1949 | Rehberg | 260/410.9 N |
| 2,503,699 | 4/1950 | Adelson | 526/227 |
| 2,573,701 | 11/1951 | Filachione | 560/185 |
| 2,659,697 | 11/1953 | Wayo | 252/56 R |
| 4,036,984 | 7/1977 | Takahashi | 424/311 |
| 4,085,277 | 4/1978 | Harada | 544/27 |

FOREIGN PATENT DOCUMENTS

| | | | |
|---|---|---|---|
| 130438 | 11/1946 | Australia | 560/266 |
| 134044 | 11/1946 | Australia | 560/266 |
| 594800 | 11/1947 | United Kingdom | 560/266 |
| 900666 | 7/1962 | United Kingdom | 560/266 |

OTHER PUBLICATIONS

Morrison, "Derivatives of Carboxylic Acids", *Organic Chemistry*, Chapter 17, p. 476, 1959.

*Primary Examiner*—Bruce Gray
*Attorney, Agent, or Firm*—Majestic, Parsons, Siebert & Hsue

[57] ABSTRACT

A method for synthesizing an acyloxycarboxylic acid by providing a reaction chamber, establishing sources of an α-hydroxycarboxylic acid and an acid chloride, and repeatedly contacting substantially equal molar amounts of the α-hydroxycarboxylic acid and the acid chloride within the reaction chamber. The acyloxycarboxylic acid so synthesized is useful as a starting material for conversion to various esters which, when placed in aqueous solution with a source of hydrogen peroxide, result in a peracid and are useful for bleaching applications.

13 Claims, No Drawings

METHOD FOR SYNTHESIZING ACYLOXYCARBOXYLIC ACIDS

This is a continuation of application Ser. No. 07/409,279, filed Sept. 19, 1989, now abandoned which was a continuation of application Ser. No. 07/167,544, filed Mar. 14, 1988, now abandoned.

FIELD OF THE INVENTION

The present invention relates to acyloxycarboxylic acids prepared by an alcoholysis reaction, and particularly a method for synthesizing acyloxycarboxylic acid in high yields. The synthesized acids are usefully converted to derivatives such as esters for bleaching applications.

BACKGROUND OF THE INVENTION

Esters of acyloxycarboxylic acids have long been known for a wide variety of applications. Thus, for example, U.S. Pat. No. 2,464,992, issued Mar. 22, 1949, inventors Rehberg et al. teaches several methods for obtaining acyloxycarboxylic acid esters from starting materials such as glycolic or lactic acid with the esters useful as solvents, plasticizers, insecticides, insect repellents and chemical intermediates. An acyloxy acetic acid is disclosed as imparting excellent rust preventing characteristics to hydrocarbon mineral oils by U.S. Pat. No. 2,659,697, issued Nov. 17, 1953, inventor Wayo.

More recently, U.S. Pat. No. 4,085,277, issued Apr. 18, 1978, inventor Harada, discloses preparation of 2-cinnamoyloxyacetic acid as a starting compound in the preparation of a cephaloaporanic acid derivative possessing antibacterial activity.

Pending application Ser. No. 928,070, entitled "Glycolate Ester Peracid Precursors", filed Nov. 6, 1986, now U.S. Pat. No. 4,778,618 inventors Fong et al., of common assignment herewith, discloses compounds termed alkanoyloxyperacetic acid which are generated in situ when precursors are placed in aqueous solution with a source of hydrogen peroxide. These precursors are readily prepared from the acyloxycarboxylic acids synthesized by the present invention.

U.S. Pat. No. 2,503,699, issued Apr. 11, 1950, inventors Adelson et al., discloses the reaction of 1.9 equivalents acetyl chloride with 1.0 equivalent glycolic acid in a single reaction vessel to obtain acetylglycolic acid, which was isolated by evaporating excess actyl chloride. However, the inventors report that the reaction was violent and evolved much hydrochloric acid. Acid chloride removal by evaporation to isolate product is not appropriate for longer chain acid chlorides.

U.S. Pat. No. 4,036,984 discloses adding various chlorides slowly under ice cooling into mixtures of various acids or alcohols with the mixtures including pyridine. However, when these known techniques are applied to the synthesis of acyloxycarboxylic acids such as, for example, octanoyloxyacetic acid, isolated yields of only about 40% to about 45% are obtained.

SUMMARY OF THE INVENTION

It is an object of the present invention to provide a method for synthesizing acyloxycarboxylic acids simply and in high yields, which acids are usefully converted to alkanoyloxyperacetic acids via ester precursors.

In one aspect of the present invention, a method for synthesizing an acyloxycarboxylic acid, useful as a starting material for conversion to various esters, comprises providing a reaction chamber, establishing sources of an α-hydroxycarboxylic acid and an acid chloride, and repeatedly contacting substantially equimolar amounts of the o-hydroxycarboxylic acid and the acid chloride within the reaction chamber. The sources of α-hydroxycarboxylic acid and acid chloride are separated from one another, and are preferably repeatedly contacted at a predetermined, relatively slow rate within the reaction chamber. However, if the mixture within the reaction chamber is sufficiently agitated and cooled, then the α-hydroxycarboxylic acid and acid chloride reactants can be contacted at relatively rapid rates.

The reaction chamber includes a basic component in an effective amount to neutralize a hydrogen chloride by-product during formation of the reaction product. The reaction product of this method is typically isolatable as at least about 65% of theoretical yield and has the structure

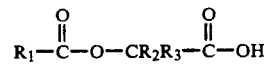

wherein $R_1$ is an alkyl group having two to about twelve carbon atoms, and $R_2$ is hydrogen, methyl, ethyl, or propyl and $R_3$ is hydrogen, methyl, ethyl, propyl, and substituted or unsubstituted phenyl or benzyl.

In another aspect of the present invention, the just described reaction product, whether isolated or not, is converted to an ester which, when placed in aqueous solution with a source of hydrogen peroxide, results in a peracid having the structure (where $R_1$, $R_2$ and $R_3$ are as previously described):

DETAILED DESCRIPTION OF THE PREFERRED EMBODIMENTS

U.S. Patent application Ser. No. 928,070, entitled "Glycolate Ester Peracid Precursors", inventors Fong et al., filed Nov. 6, 1986, and U.S. Ser. No. 928,065, titled "Acyloxynitrogen Peracid Precursors", inventor Zielske, filed November 6, 1986, both assigned to The Clorox Company, are both incorporated herein by reference as disclosing ester conversions and applications useful with the present invention. The former application, for example, discloses preparations of acyloxycarboxylic acids which are converted to esters and utilized in bleach compositions to generate peracid when placed in aqueous solution with a source of hydrogen peroxide. However, the present inventive method provides acyoxycarboxylic acid preparations in considerably higher yields than disclosed.

Thus, Example I of Patent application Ser. No. 928,070 describes a synthesis of octanoyloxyacetic acid from glycolic acid and octanoyl chloride. The octanoyl chloride was added dropwise by means of an addition funnel to a flask charged with glycolic acid in chloroform and triethylamine with a minor amount of 4-dimethylaminopyridine. Isolated yield of the octanoyloxyacetic acid (with 90% purity) was 40% of theoretical yield. By contrast, and as described more fully hereinafter, isolated yield of octanoyloxyacetic acid (with greater than 90 wt. % purity) from practice of the present invention is at least about 65% of theoretical yield, and typically is greater than about 80 mole % crude yield.

Attempts to adapt the previously discussed Adelson et al. method from acetyl chloride (at 1.9 equivalents) with glycolic acid (at 1.0 equivalent) to a longer chain acid chloride, such as octanoyl chloride, result in an octanoyloxyacetic acid isolated yield of only 45%, by comparison to the above noted at least about 65% isolated yield in accordance with the present invention.

The disappointingly low isolated yields of desired acyloxycarboxylic acids by previously known methods are believed due, at least in part, to the bifunctional nature of alpha-hydroxycarboxylic acids since the acid chloride can react with either (or both) of the hydroxyl moieties. Practice of the inventive method is believed substantially to avoid the problems incurred with previous methods. That is, the present invention avoids the relatively low overall yields of reaction product, avoids the use of large excess of expensive starting material and avoids difficulty in isolation of the desired reaction product.

Practice of the inventive method typically provides the desired acyloxycarboxylic acid in about 80% to 85% crude yield, substantially avoids complicating side reactions such as generation of polygycolic acid, and permits the desired reaction product to be readily isolated (if desired).

Practice of the inventive method synthesizes an acyloxycarboxylic acid, or reaction product, having the structure illustrated by Formula I below.

FORMULA I

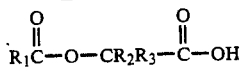

The $R_1$ substituent of the Formula 1 structure may be selected from alkyl groups (branched and unbranched) having two to about twelve carbon atoms, that is from ethyl, propyl, butyl, pentyl, hexyl, heptyl, octyl, nonyl decyl, undecyl, and dodecyl groups. The $R_2$ substituent of the Formula I structure may be hydrogen or a lower alkyl group having one to about three atoms. The $R_3$ substituent may be a lower alkyl, such as methyl, ethyl or propyl, an aryl, such as phenyl or benzyl groups, or an alkylaryl, such as tolyl or xylyl.

This acyloxycarboxylic acid reaction product is formed by an alcoholysis reaction of an alpha-hydroxycarboxylic acid and an acid chloride in a reaction chamber. The total quantity of each reactant to be reacted in the reaction chamber is sometimes hereinafter referred to as an alpha-hydroxycarboxylic acid source and an acid chloride source. These reactant sources are a spaced distance from the reaction chamber and are separated from one another. This will be discussed more fully hereinafter.

Suitable alpha-hydroxycarboxylic acids for use as reactants in the inventive method include glycolic acid, lactic acid and the like, with some suitable such acids being illustrated by Table I.

TABLE I

| Acid Name | Structure |
|---|---|
| Glycolic | $HOCH_2\overset{O}{\overset{\|}{C}}OH$ |
| Lactic | $HO\overset{}{\underset{CH_3}{C}}H\overset{O}{\overset{\|}{C}}OH$ |
| 2-hydroxy butyric | $HO\overset{}{\underset{C_2H_5}{C}}H\overset{O}{\overset{\|}{C}}OH$ |
| α-hydroxy isobutyric | $HO-\overset{CH_3}{\underset{CH_3}{C}}-\overset{O}{\overset{\|}{C}}OH$ |
| Mandelic | $HO\overset{}{\underset{\phi}{C}}H\overset{O}{\overset{\|}{C}}OH$ |
| β-phenyl lactic | $HO\overset{}{\underset{\underset{\phi}{CH_2}}{C}}H\overset{O}{\overset{\|}{C}}OH$ |
| 2-hydroxy-2-methyl-butyric | $HO-\overset{CH_3}{\underset{C_2H_5}{C}}-\overset{O}{\overset{\|}{C}}OH$ |
| α-hydroxy isocaproic | $HO-\overset{CH_3}{\underset{C_3H_7}{C}}-\overset{O}{\overset{\|}{C}}OH$ |

Glycolic acid is particularly preferred due to low cost, ready availability and suitable solubilities of the esters.

Suitable acid chlorides for use as reactants have the structure illustrated by Formula II below, where $R_1$ is an alkyl group (branched or unbranched) having 2 to about 12 carbon atoms.

FORMULA II

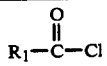

Preferred acid chlorides are hexanoyl chloride, octanoyl chloride, heptanoyl chloride, nonanoyl chloride decanoyl, undecanoyl, and dodecanoyl chloride. Particularly preferred are octanoyl and nonanoyl chlorides.

It is extremely important that the alpha-hydroxycarboxylic acid and the acid chloride reactants be reacted by contacting substantially equimolar amounts within the reaction chamber. Excesses of one or the other components reduce selectivity of the desired reaction and thus reduce yield (illustrated as Reaction I below). For example, an excess of an acid reactant such as glycolic acid favors production of polyglycolates. An excess of the acid chloride reactant tends to lead to diketene formation.

The reaction is preferably conducted by contacting relatively small portions of the total reactant quantities in the reaction chamber. This may be achieved by pumping equimolar, metered quantities of both reactants (either neat or in solution) from the respective sources at a predetermined rate into the reaction chamber, and thus repeatedly contacting substantially equimolar amounts of the alpha-hydroxycarboxylic acid and the acid chloride.

This continuous and controlled reaction has been found substantially to prevent formation of a mixed anhydride as reaction product and thus to retard formation of undesired esters. For convenience, the reaction in which the acyloxycarboxylic acid is formed is illustrated as Reaction I.

REACTION I

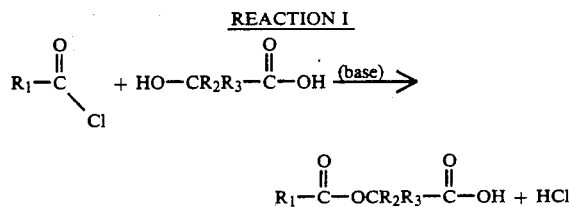

The contents of the reaction chamber are preferably agitated during the repeated contact of reactants, and a predetermined rate of pumped, metered quantities of reactants may be from about 0.1 to about 10.0 mole per liter per hour, more preferably about one mole per liter per hour for each reactant. However, as will be understood, the particular predetermined rate will be dependent upon the reaction vessel geometry, the mixing efficiency, and the heat exchanging capacity of the system being used. Means known to the art, such as metering pumps for each reactant source, are a convenient way to pump such controlled quantities at the predetermined rate. The reaction is exothermic, and thus the reaction chamber is preferably cooled during the reaction by means well known to the art.

Where the alpha-hydroxycarboxylic acid is a solid, then a solvent is desirable to solubilize the alpha-hydroxycarboxylic acid within the reaction chamber during the repeated contact with the acid chloride. Suitable solvents are aprotic, polar and vary from water immiscible to water miscible, and preferably do not generate much heat from solvation. Preferred solvents are acetone, dichloromethane, acetonitrile, methyl ethyl ketone, diethyl ether, tetrahydrofuran, glyme, dioxane and ethyl acetate, most preferably acetone. The solvent is preferably present within the alpha-hydroxycarboxylic acid source, so that solubilized quantities can be conveniently flowed to the reaction chamber. Solvents may also be present within the reaction chamber to facilitate agitation and cooling of the reaction mixture.

During the reaction, the reaction chamber preferably includes a basic component. A suitable base is in an effective amount to neutralize the hydrogen chloride by-product that forms as the reaction proceeds. Suitable bases are believed to perform a dual function in not only neutralizing the hydrogen chloride by-product, but in apparently also acting to promote or catalyze the reaction. Preferred bases are tertiary amines such as pyridine, dimethylaminopyridine, triethylamine, t-propylamine, N-methylpiperidine and polymeric tertiary amines or cross-linked resins, such as polyvinylpyridine divinylbenzene, BIO-REX5 intermediate base anion exchange resin, AG4-X4 or AG3-X4A weakly basic anion exchange resin (the latter three being available from BIO-RAD Laboratories). The base preferably is used in about a stoichiometric amount (with respect to the reactants illustrated in Reaction I), and must not react with the acid chloride reactant.

The acyloxycarboxylic acid reaction product is contemplated for use as a bleach precursor having the general structure illustrated by Formula III.

FORMULA III

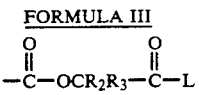

where $R_1$ and $R_2$ are as previously described, and L is a leaving group. The carbonyl carbon of Formula III adjacent the leaving group is preferably esterified, and will have the leaving group bonded through the ester linkage.

Suitable leaving groups include derivatives of substituted or unsubstituted phenols, oximes, N-hydroxyimides, and amine oxides. These various suitable leaving groups are more fully described in previously noted application Ser. No. 928,065 and application Ser. No. 928,070.

The conversion of reaction product, prepared in accordance with the invention, to an ester is preferably via an acid chloride of the reaction product, as will be exemplified hereinafter. Such an ester, or bleach precursor, is usefully formulated with a solid source of peroxide, such as an alkaline peroxide, in amount effective to perhydrolyze the precursor and thus to provide effective bleaching. Suitable such sources of peroxide include sodium perborate monohydrate, sodium perborate tetrahydrate, sodium carbonate peroxyhydrate, sodium pyrophosphate peroxyhydrate, urea peroxyhydrate, sodium peroxide, and mixtures thereof. Sodium perborate monohydrate and sodium perborate tetrahydrate are particularly preferred alkaline peroxides for combination with such precursors as a dry bleach composition or, when surfactant is included, as a dry laundering and bleaching composition.

The source of peroxide (that is, compounds yielding hydrogen peroxide in an aqueous solution) itself constitutes a peroxygen bleaching compound. However, bleach compositions including peroxyacid precursor and peroxide source together provide better bleaching, particularly at temperatures below about 60° C., than the peroxide source alone.

Two preferred bleach compositions including glycolate esters prepared in accordance with the inventive method are illustrated below.

| | |
|---|---|
| 15.6% | sodium perborate tetrahydrate |
| 19.0% | octanoyloxy acetic acid, p-phenyl sulfonate ester |
| 7.0% | nonionic surfactant |
| 15.0% | sodium carbonate |
| 43.4% | sodium sulfonate |
| 100.0% | |
| | |
| 15.5% | sodium perborate tetrahydrate |
| 16.8% | octanoyloxy acetic acid, t-butyl phenol ester |
| 7.0% | nonionic surfactant |
| 15.0% | sodium carbonate |
| 45.7% | sodium sulfate |
| 100.0% | |

EXAMPLE I

Synthesis of Octanoyloxy Acetic Acid (OOAA)

15.8 gm (0.20 mole) pyridine and 50 ml. acetone were combined in a 250 ml. round bottomed-three necked flask equipped with magnetic stir bar and two addition funnels, and cooled in an ice water bath with stirring. One addition funnel was charged with 15.5 gm (0.20 mole) glycolic acid dissolved in approximately 75 ml. acetone. The other addition funnel was charged with 32.5 gm (0.20 mole) octanoyl chloride. The contents of each addition funnel were added simultaneously to the cooled, stirred pyridine solution so that the complete addition of each component was continuous over one hour. The resultant slurry (a precipitation of pyridine hydrochloride was noted) was stirred an additional 45 minutes at ice bath temperature, and then at room temperature for another 30 minutes. Solvent was then removed by rotary evaporation at reduced pressure and 45C. The residual oil was dissolved in 200 ml dichloromethane and this was extracted with 3×150 ml. of 4% aqueous HCl. The dichloromethane layer was dried over sodium sulfate, decanted and the solvent removed by rotary evaporation. Drying on high vacuum for 4 hours left OOAA and 8.0% octanoic acid by weight, giving a crude yield for OOAA of 84%(mole). Recrystallization from 200 ml. hexane gave 27 g of a white crystalline product melting at 50 to 52° C., which was determined to be 99% wt. OOAA, giving a 67% (mole) yield of pure octanoxyloxyacetic acid.

EXAMPLE II

Synthesis of Octanoxyloxy Acetyl Chloride 101.1 gm (0.5 mole) octanoyloxy acetic acid and 83 gm (0.65 mole) oxalyl chloride are combined in a 1 liter round bottom flask with a magnetic stir bar and a $CaSO_4$ drying tube (note: a little hexame or petroleum ether can be added if the solid does not completely dissolve). The reaction is stirred at room temperature while rapid gas evolution is noted, then gradually heated to 40-50° C. and held there for 2 hours, then at 65-70° C. for one hour (note: the reaction can also be run at room temperature overnight with the advantage that it remains colorless). The slightly yellow solution is then heated to 60-70° C. under aspirator pressure for one to 1½ hours to remove excess oxalyl chloride. After cooling to room temperature the oil is diluted with 400 ml petroleum ether (bp 30-60° C.) and extracted with 3×200 ml ice water (caution: gas evolution can be vigorous!). The organic layer is dried over $MgSO_4$, filtered and roto vapped to a clear straw colored oil, weight =115.7 gm (110.4 gm theoretical). IR shows no acid-OH stretch and two carbonyls at about 1,812 $cm^{-1}$ and at about 1,755 $cm^{-1}$.

EXAMPLE III

Synthesis of Octanoyloxy Acetic Acid, Phenyl Sulfonate Ester 17.3 gm (.079 mole) octanoyloxy acetyl chloride and 17.0 gm (.087 mole) sodium-p-phenol-sulfonate (dried at 120° C. in vacuo for 16 hours) were combined in a 250 ml round bottom flask with a magnetic stir bar. 30 ml of ethylene glycol-dimethyl ether (glyme) was added, and the slurry stirred with cooling in an ice-water bath. 7.8 gm (0.077 mole) triethyl amine was placed in an additional funnel equipped with a $CaSO_4$ drying tube and this was added dropwise to the above slurry over ½ hour. The reaction becomes very thick and more glyme (or ethyl ether) can be added at this time to enable good stirring. The reaction was stirred for two hours at room temperature, diluted with ethyl ether and stirred one hour more. The reaction was filtered on a coarse glass frit, washed with several portions of ethyl ether, sucked dry for one hour and dried in vacuo at room temperature. Weight of product: 39 gm (theoretical wt.=42.1 gm).

This material can be recrystallized from 60/40 (vol/-vol) IpA/water in an approximate 3 to 4:1 (wt./wt.) ratio of solvent to ester reaction mixture to give an approximate 40-60% yield of ester (90+% in purity).

EXAMPLE IV

Synthesis of Hexanoyloxy Acetic Acid 10.1 gm (0.10 mole) triethyl amine (TEA), 10 drops of pyridine, and 15 ml acetone were combined in a 250 ml round bottomed, three-necked flask equipped with magnetic stir bar and two addition funnels, and cooled in an ice water bath with stirring. One addition funnel was charged with 7.61 gm (0.10 mole) glycolic acid dissolved in 30 ml acetone. The other funnel was charged with 13.5 gm (0.10 mole) hexanoyl chloride. The contents of each addition funnel were added simultaneously to the cooled, stirred TEA/pyridine solution so that the complete addition of each component was continuous over 20 minutes (note: a heavy white precipitate, presumably TEA hydrochloride, formed during the addition). The reaction was stirred an additional one hour, filtered and the isolated salts washed with acetone, which was combined with the initial filtrate. Solvent was removed by rotary evaporation leaving a sweet smelling oil, which was dissolved in 150 ml diethyl ether, and extracted with 2×200 ml of 1% aqueous HCl. The ether layer was dried over magnesium sulfate, filtered and rotary evaporated to an oil weighing 20 gm of 74% wt. purity by GC, for a yield of 85% mole. No hexanoic or glycolic acids were found in the product, which was used without further purification.

EXAMPLE V

Synthesis of Hexanoyloxy Acetic Chloride 8.7 gm (0.05 mole) of hexanoylacetic acid and 12.7 gm (0.10 mole) of oxalyl chloride were mixed together at room temperature. The reaction was heated gradually over one hour at 50-60° C. for about two hours. Excess oxalyl chloride was removed under reduced pressure to yield an oil that exhibits no —OH stretch by IR. Weight was 9.6 gm.

EXAMPLE VI

Synthesis of Sodium, n-Hexanoyloxyacetate, p-phenylsulfonate 9 2 gm (0.04 mole) of n-hexanoyloxyacetyl chloride was added dropwise to an ice-cooled slurry of 9.0 gm (0.046 mole) sodium, p-phenolsulfonate (dried four hours at 110° C. in vacuo) and 5.5 gm (0.045 mole) triethylamine in 45 ml diglyme in a 100 ml round bottom flask fitted with a stirrer and low temperature thermometer. The reaction mixture was stirred for two hours at 0-4° C., diluted with 100 ml ethyl ether, and filtered.

The white solid precipitate was triturated with 3×100 ml of warm isopropanol and the solid was vacuum filtered and dried overnight under vacuum.

EXAMPLE VII

Synthesis of Octanyloxyacetate, T-butyl Phenol Ester 5.95 gm (.025 mole) octanoyloxyacetyl chloride dissolved in about 15 ml anhydrous ethyl ether was added dropwise to a solution containing 2½ gm (0.027 mole) pyridine and 4.70 gm (.031 mole) t-butyl phenol in about 100 ml pyridine over one-half hour, with the solution being maintained at a temperature of 0–4° C. in an ice bath and stirred via a magnetic stir bar. The reaction was stirred at 5–10° C. for about 2 hours, filtered and then diluted to about 200 ml with ethyl ether. This was washed with 3 times 100 ml of 4% hydrochloric acid, 1 times 150 ml water, 2 times 100 ml of 10% sodium carbonate solution, then dried over sodium sulfate. The product was filtered and roto-vapped to yield a yellow oil, which was chromatographed on 60 gm of silica gel with 4% ethyl ether/petroleum ether distillate, yielding 5.3 gm of ester product determined to be 99.9 wt. % in purity by GC, saponification and NMR-13C.

EXAMPLE VIII

Synthesis of Mixed Octanoyloxy/Decanoyloxy Acetic Acids

Reaction 1: 156.5 gm (1.01 equivalents) of $C_8/C_{10}$ mixed aliphatic acids (63 mole % $C_8$ and 37 mole % $C_{10}$) and 114 ml (approx. 165 gm, 1.3 mole) oxalyl chloride were combined in a 1000 ml round bottomed flask equipped with a magnetic stir bar and a calcium sulfate drying tube. The resultant solution was stirred for 19 hours (note: vigorous gas evolution ensued upon mixing of the two reactants). Excess oxalyl chloride was removed by warming of the reaction under reduced pressure for one hour. The residue was taken up in 300 ml of hexane and this solution was extracted with 5×250 ml of ice cold water. The hexane layer was dried over sodium sulfate, filtered and the solvent removed by rotary evaporation, leaving 184.5 gm of light straw colored oil. (No —OH by IR, and a strong $v_{C=O}$ at 1,803 cm).

Reaction 2: A two liter, three-necked round bottom flask, equipped with mechanical stirrer and two addition funnels, was flame dried and charged with 79.5 gm (1.0 mole) pyridine in 200 ml acetone, which was then chilled in an ice water bath. One addition funnel was charged with the product from reaction 1 above, and the other charged with 84 gm (1.1 mole) glycolic acid in 300 ml acetone. The contents of the two addition funnels were added simultaneously and continuously to the stirred, chilled pyridine solution over 50 minutes. The reaction was then stirred an additional 2½ hours at ice bath temperature. Solvent was removed by rotary evaporation and the oily residue dissolved in 50 ml dichloromethane, which solution was then extracted with 5×350 ml 5% aqueous HCl and 1×600 ml saturated NaCL, dried over sodium sulfate, filtered and rotary evaporated to a thick oil which soldified upon standing. Pumping off the residual solvent under high vacuum left 199 gm of solid which was determined to be 54.7% mole octanoyloxy acetic acid and 34.1% mole decanolyoxy acetic acid by GC. Overall yield of the two step reaction was 83.4% mole for the combined acyl oxy acetic acids.

EXAMPLE IX

Synthesis of Mixed Octanoyl/Decanoyl-Oxyacetic Acids, Sodium Phenol Sulfonate Esters 198 g of mixed octanoyl/decanoyl oxyacetic acids from Example VIII were melted on a warm (50° C.) oil bath in a 1,000 ml round bottom flask. 113 ml of oxalyl chloride were added to the liquified acids and the reaction stirred by magnetic stir bar overnight at room temperature. The reaction was then warmed to 50° C. on an oil bath and excess oxalyl chloride removed at water aspirator pressure for 3½ hours. The oily residue was dissolved in 700 ml hexane and washed with 3×250 ml of ice cold water. The hexane layer was dried over $Na_2SO_4$, filtered, and rotary evaporated to a light yellow oil weighing 219 gm·IR of this material exhibited no —OH stretch and C=O stretch at 1,760 cm$^{-1}$ and 1,820 cm$^{-1}$. These acid chlorides were then esterified as follows:

219 gm of the acid chlorides, 220 gm of sodium phenol sulfonate (from di-hydrate dried in vacuo at 120° C. for 48 hours), and 800 ml of anhydrous glyme were combined in a flame dried 2½ necked Morton flask, equipped with a mechanical stirrer and addition funnel, and placed in an ice-water bath. The addition funnel was charged with 120 gm of triethyl amine, which was added dropwise over one hour to the rapidly stirred, cooled acid chloride/phenol slurry. Over the time of addition of the amine the reaction mixture became so thick that an additional 500 ml of glyme was added to enable efficient stirring to proceed. Upon completion of the amine addition the reaction was stirred ½ hour longer, by which time it had become unstirrable. The reaction was allowed to stand two hours, and then filtered on a C-frit Buchner funnel. The filter cake was washed with 1,000 ml of ethyl ether and sucked dry overnight. The residue was dried in vacuo leaving 470 gm of off-white powder, which contained 62% wt. of the desired esters, corresponding to a 74% mole conversion based on the starting ($C_8/C_{10}$) acid mixture. After two recrystallizations from (approximately 1,200 to 1,800 ml each) 194 gm. of 95.7% wt. of the desired esters was obtained. Overall yield from the starting acids was 54% mole for the four reaction steps (Examples VIII and IX). The product contained less than 1.0% each of the $C_8/C_{10}$ acyl-oxy acetate benzene sulfonate esters (HPLC).

EXAMPLE X

Synthesis of 2-Hexanoyloxy-2-Methyl-Butryic Acid 11.8 gm (0.10 mole) 2-methyl-2-hydroxy-butyric acid was dissolved in 50 ml acetone and placed in one of two 125 ml addition funnels attached to a 250 ml three-necked round bottom flask charged with 8.0 gm (0.10 mole) pyridine in 50 ml acetone cooled in an ice-water bath. The other addition funnel was charged with 13.46 gm (0.10 mole) hexanoyl chloride. The contents of the two addition funnels were simultaneously added dropwise over 20 minutes to the stirred/cooled pyridine solution. The reaction was then stirred for two hours at 4–15° C., then the solvent was removed by rotary evaporation. The oily residue was dissolved in 200 ml dichloromethane and this solution extracted with 5×150 ml 3% aqueous HCl, then washed with 1×200 ml deionized water. The organic layer was dried over $Na_2SO_4$, filtered and solvent removed by rotary evaporation, leaving 20.4 gm of light yellow oil (IR shows $V_{C=O}$ at 1,745 and 1,728 cm$^{-1}$). $^{13}$C NMR saponification and GC analysis shows this material to be 99% the desired product, for an overall yield of 93%.

EXAMPLE XI

Synthesis of 2-Octanoyl-Mandelic Acid 15.2 gm (0.10 mole) dl-mandelic acid was dissolved in 50 ml acetone and placed in one of two 125 ml additional funnels attached to a 250 ml three-necked round bottom flask charged with 8.0 gm (0.10 mole) pyridine in 50 ml acetone cooled in an ice water bath. The other addition funnel was charged with 16.3 gm (0.10 mole) octanoyl chloride. The contents of the two addition funnels were simultaneously added dropwise over 20 minutes to the stirred/cooled pyridine solution. The reaction was removed by rotary evaporation. The residue was dissolved in 200 ml diethyl ether and this solution was extracted with 5×150 ml 5% HCl, and then washed with 1×200 ml deionized water. The organic layer was dried over Na$_2$SO$_4$, filtered and the solvent removed by rotary evaporation. After drying in vacuo there remained 28.2 gm of oil. GC and $^{13}$C NMR determined this material to be 83.1% of the desired product, for an overall 84.2% yield.

EXAMPLE XII

Synthesis 2-Hexanoyl Mandelic Acid 15.2 gm (0.10 mole) dl-mandelic acid was dissolved in 50 ml acetone and placed in one of two 125 ml additional funnels attached to a 250 ml three-necked round bottom flask charged with 8.0 gm (0.10 mole) pyridine in 50 ml acetone cooled in an ice water bath. The other addition funnel was charged with 13.46 gm (0.10 mole) hexanoyl chloride. The contents of the two addition funnels were simultaneously added dropwise to the stirred, cooled pyridine solution. The reaction was then stirred at room temperature for two hours, at which time the solvent was removed by rotary evaporation. The oily residue was dissolved in 200 ml CH$_2$Cl$_2$, and this solution was extracted with 4×150 ml 3% aqueous HCl, and washed with 1×200 ml deionized water. The organic layer was dried over Na$_2$SO$_4$, filtered and the solvent removed by rotary evaporation, and dried in vacuo leaving 24.9 gm of oil. $^{13}$C NMR and GC analysis determined this material to be 89.5% desired product, for an overall 89% yield.

Preparation of an oxime derivative is preferably by obtaining an acid chloride (illustrated by Example II and Example V), reacting with acetone oxime in a solvent such as THF dropwise with rapid stirring, in a manner analogous to Example I of previously noted application Ser. No. 928,065. The acyloxycarboxylic acids just exemplified by Examples I, Iv, VIII, X, XI and XII are summarized by Table II.

TABLE II

| Example | Acid Prepared | Crude Yield (mole %) |
|---|---|---|
| I | C$_7$H$_{15}$C(=O)—O—CH$_2$—C(=O)OH | 84 |
| IV | C$_5$H$_{11}$C(=O)—OCH$_2$—C(=O)—OH | 85 |
| VIII | C$_7$H$_{15}$C(=O)—OCH$_2$C(=O)OH and C$_9$H$_{19}$C(=O)—OCH$_2$C(=O)OH | 83.4 |
| X | C$_5$H$_{11}$CO(=O)—C(CH$_3$)(C$_2$H$_5$)—C(=O)OH | 93.0 |
| XI | C$_7$H$_{15}$C(=O)—O—CH(C$_6$H$_5$)—C(=O)—OH | 84.3 |
| XII | C$_5$H$_{11}$C(=O)—O—CH(C$_6$H$_5$)—C(=O)OH | 89.0 |

As may be seen from Examples I, Iv, VIII, X, XI and XII, yield of crude acid products prepared by the inventive method ranged from 83.4% to 93%. While these acyloxycarboxylic acids may then be isolated before conversion to an ester for use as a bleach precursor, such isolation is often not necessary. Example II illustrates use of an isolated acyloxycarboxylic acid (prepared as in Example I) to the chloride derivative and Example III illustrates conversion of such chloride to the p-phenyl sulfonate ester; however, Examples VIII and IX illustrate preparation of ester derivatives without an isolation of acyloxycarboxylic acid. Thus, the present invention provides a method for synthesizing acyloxycarboxylic acids simply and in high yields, which acids are usefully converted (without or without isolation) to ester precursors of alkanoyloxy peracetic acids.

Although the present invention has been described with reference to specific examples, it should be understood that various modifications and variations can be easily made by those skilled in the art without departing from the spirit of the invention. Accordingly, the foregoing disclosure should be interpreted as illustrative only and not to be interpreted in a limiting sense. The present invention is limited only by the scope of the following claims.

It is claimed:

1. A method for synthesizing an acyloxycarboxylic acid comprising:
    providing a reaction chamber, the reaction chamber including a basic component in an amount effective to neutralize HCl by-product during formation of a reaction product;
    establishing sources of an α-hydroxy carboxylic acid and an acid chloride, both sources being separated from the reaction chamber and separated from one another; and repeatedly and simultaneously contacting substantially equimolar amounts of the α-hydroxy carboxylic acid and the acid chloride within the reaction chamber from the sources thereof, wherein neither reactant is present in a significant excess over the other, to form an isolatable reaction product within the reaction chamber, the repeated and simultaneous contacting including introducing predetermined equimolar quantities at a predetermined rate of the α-hydroxy carboxylic acid and the acid chloride from the sources thereof into the reaction chamber, the predetermined quantities being small relative to total reactant quantities that accumulate in the reaction chamber, the reaction product having the structure

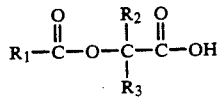

wherein $R_1$ is an alkyl group having two to about twelve carbon atoms, $R_2$ is hydrogen, a methyl, ethyl or propyl group, and $R_3$ is hydrogen, a methyl, ethyl or propyl group, or an alkyl substituted or unsubstituted benzyl or phenyl group.

2. The method as in claim 1 wherein the basic component is a tertiary amine.

3. The method as in claim 1 wherein the basic component includes pyridine, dimethylaminopyridine, triethylamine, t-propylamine, N-methylpiperdine or a polymeric tertiary amine.

4. The method as in claim 1 further comprising:
isolating the reaction product from the reaction chamber, the isolated reaction product being at least about 65% of theoretical yield.

5. The method as in claim 4 wherein contents of the reaction chamber are agitated during the simultaneous contact of a α-hydroxy carboxylic acid and acid chloride.

6. The method as in claim 1 wherein the α-hydroxy carboxylic acid is solubilized within the reaction chamber during the repeated contact with the acid chloride.

7. The method as in claim 6 wherein the α-hydroxy carboxylic acid is solubilized by an effective amount of an aprotic solvent.

8. The method as in claim 1 wherein the α-hydroxy carboxylic acid includes glycolic acid, lactic acid, α-hydroxy propionic acid, α-hydroxy isobutyric acid, 2-hydroxy butyric acid, mandelic acid, β-phenyl lactic acid, 2-hydroxy-2-methyl butyric acid or α-hydroxy isocaproic acid.

9. The method as in claim 8 wherein the acid chloride is selected from hexanoyl chloride, octanoyl chloride, decanoyl chloride, nonanoyl chloride and heptanoyl undecanoyl and dodecanoyl chloride.

10. The method as in claim 1 wherein the predetermined rate is about one M per hour.

11. A method for synthesizing a bleach precursor comprising:
providing a reaction chamber, the reaction chamber including an effective amount of base to neutralize HCl by-product;
establishing sources of an α-hydroxy carboxylic acid and an acid chloride, both sources being a spaced distance from the reaction chamber and separated from one another;
simultaneously contacting substantially equimolar amounts of the α-hydroxy carboxylic acid and the acid chloride by delivering at a predetermined flow rate from the sources thereof, wherein neither reactant is present in a significant excess over the other, into the reaction chamber to form a reaction product and HCl by-product, the reaction product being an acyloxycarboxylic acid; and
converting the reaction product to an ester.

12. The method as in claim 11 wherein the ester conversion includes converting the reaction product to a corresponding acid chloride.

13. The method as in claim 11 wherein the ester has the structure

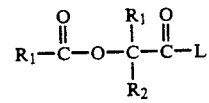

wherein $R_1$ is an alkyl group having two to above twelve carbon atoms, $R_2$ is hydrogen, a methyl, ethyl or propyl group, and $R_3$ is hydrogen, a methyl, ethyl or propyl group, a benzyl or phenyl group, or a benzyl or phenyl group substituted on the ring thereof with a methyl or ethyl group, and L is a derivative of a substituted or unsubstituted phenol, the substituent being one or more of a sulfonate, a sulfate, a carbonate, a quaternary nitrogen, an alkoxy of about 1 to 10 carbons, or an alkyl of about 1 to 6 carbons, an oxime, a N-hydroxyimide or an amine oxide.

* * * * *

UNITED STATES PATENT AND TRADEMARK OFFICE
CERTIFICATE OF CORRECTION

PATENT NO. : 5,091,560
DATED : February 25, 1992
INVENTOR(S) : Richard R. Rowland It is certified that error appears in the above-identified patent and that said Letters Patent is hereby corrected as shown below:

Column 14, line 40, in Claim 13      delete "above"
                                     insert---about---

Signed and Sealed this

Fourth Day of May, 1993

*Attest:*

MICHAEL K. KIRK

*Attesting Officer*       *Acting Commissioner of Patents and Trademarks*